(12) United States Patent
Chang et al.

(10) Patent No.: US 6,673,087 B1
(45) Date of Patent: Jan. 6, 2004

(54) ELONGATED SURGICAL SCISSORS

(75) Inventors: Tenny Chang, Mountain View, CA (US); Charles Gresl, San Francisco, CA (US); John Lunsford, San Carlos, CA (US); Jon A. Sherman, Cincinnati, OH (US); Theodore A. Richardson, Cincinnati, OH (US)

(73) Assignee: Origin Medsystems, Menlo Park, CA (US)

( * ) Notice: Subject to any disclaimer, the term of this patent is extended or adjusted under 35 U.S.C. 154(b) by 0 days.

(21) Appl. No.: 09/739,054

(22) Filed: Dec. 15, 2000

Related U.S. Application Data

(63) Continuation-in-part of application No. 09/739,595, filed on Dec. 15, 2000, now abandoned.

(51) Int. Cl.[7] ................................................ A61B 17/32
(52) U.S. Cl. ........................ 606/174; 606/50; 606/170
(58) Field of Search ............................ 606/174, 37, 45, 606/46, 50, 51, 170, 139, 141, 142

(56) References Cited

U.S. PATENT DOCUMENTS

| | | | |
|---|---|---|---|
| 4,449,518 A | * | 5/1984 | Konomura et al. .......... 606/174 |
| 5,171,256 A | | 12/1992 | Smith et al. |
| 5,184,625 A | | 2/1993 | Cottone, Jr. et al. |
| 5,320,636 A | | 6/1994 | Slater |
| 5,324,289 A | | 6/1994 | Eggers |
| 5,338,317 A | | 8/1994 | Hasson et al. |
| 5,342,381 A | | 8/1994 | Tidemand |
| 5,352,222 A | | 10/1994 | Rydell |
| 5,356,408 A | | 10/1994 | Rydell |
| 5,366,476 A | | 11/1994 | Noda |
| 5,392,789 A | | 2/1995 | Slater et al. |
| 5,395,386 A | | 3/1995 | Slater |
| 5,396,900 A | | 3/1995 | Slater et al. |
| 5,514,134 A | | 5/1996 | Rydell et al. |
| 5,531,755 A | | 7/1996 | Smith et al. |
| 5,540,685 A | | 7/1996 | Parins et al. |
| 5,540,711 A | | 7/1996 | Kieturakis et al. |
| 5,549,606 A | | 8/1996 | McBrayer et al. |
| 5,569,243 A | | 10/1996 | Kortenbach et al. |
| 5,571,100 A | | 11/1996 | Goble et al. |
| 5,591,202 A | | 1/1997 | Slater et al. |
| 5,666,965 A | | 9/1997 | Bales et al. |
| 5,683,388 A | * | 11/1997 | Slater ........................ 606/51 |
| 5,690,606 A | | 11/1997 | Slotman |
| 5,695,521 A | | 12/1997 | Anderhub |
| 5,697,949 A | | 12/1997 | Giurtino et al. |
| 5,700,261 A | | 12/1997 | Brinkerhoff |
| 5,707,392 A | | 1/1998 | Kortenbach |
| 5,741,285 A | | 4/1998 | McBrayer et al. |
| 5,779,701 A | | 7/1998 | McBrayer et al. |
| 5,860,975 A | | 1/1999 | Goble et al. |
| 5,891,140 A | * | 4/1999 | Ginn et al. .................... 606/48 |
| 5,893,846 A | | 4/1999 | Bales et al. |
| 5,908,420 A | | 6/1999 | Parins et al. |
| 5,954,720 A | | 9/1999 | Wilson et al. |
| 5,967,997 A | | 10/1999 | Turturro et al. |
| 5,976,130 A | | 11/1999 | McBrayer et al. |
| 6,024,744 A | | 2/2000 | Kese et al. |
| 6,090,108 A | | 7/2000 | McBrayer et al. |
| 6,179,837 B1 | | 1/2001 | Hooven |
| 6,206,872 B1 | | 3/2001 | Lafond et al. |
| 6,283,963 B1 | | 9/2001 | Regula |
| 6,299,630 B1 | | 10/2001 | Yamamoto |
| 6,355,035 B1 | | 3/2002 | Manushakian |
| 6,464,701 B1 | | 10/2002 | Hooven et al. |

* cited by examiner

*Primary Examiner*—Julian W. Woo
(74) *Attorney, Agent, or Firm*—Fenwick & West LLP

(57) ABSTRACT

Surgical scissors include a pair of scissor blades mounted at a distal end of an elongated flexible body and a housing attached to the proximal end of the elongated body. An actuator is coupled with mechanical advantage to the scissor blades for manually controlling shearing movement of the blades in response to finger movement on the actuator back and forth along the housing. Electrical conductors are provided through body and housing from a connector to the scissor blades. The housing is configured to be assembled in mating shells with components assembled in and confined by attached shells that facilitate rapid and accurate fabrication.

7 Claims, 8 Drawing Sheets

ELONGATED SURGICAL SCISSORS

RELATED APPLICATION

This application is a continuation-in-part of application Ser. No. 09/739,595, entitled "Surgical Scissors and Method", filed on Dec. 15, 2000 now abandoned by T. Chang et al.

FIELD OF THE INVENTION

This invention relates to surgical scissors, and more particularly to scissors of slender design and flexible structure for endoscopic surgery with convenient manual actuation.

BACKGROUND OF THE INVENTION

Endoscopic surgery commonly requires manual manipulation of surgical instruments that are introduced into a surgical site within a patient through elongated cannulas containing one or more interior lumens of slender cross section. Endoscopic surgery to harvest a saphenous vein usually involves an elongated cannula that is advanced along the course of the vein from an initial incision to form an anatomical space about the vein as connective tissue is dissected away from the vein.

Lateral branch vessels of the saphenous vein can be conveniently isolated and ligated within the anatomical space under endoscopic visualization using surgical scissors that can be positioned and manipulated through the elongated cannula. Such surgical procedures are commonly employed in the preparation of the saphenous vein for removal from within the anatomical space for use, for example, as a shunting or graft vessel in coronary bypass surgery.

One difficulty commonly encountered using surgical scissors to ligate vessels within the confines of limited anatomical space formed along the course of the saphenous vein is that the slender configuration of surgical scissors suitable for introduction into a remote surgical site through a lumen of an elongated catheter precludes attaining much mechanical leverage for opening and closing a pair of mating scissor blades about a pivot axis. Surgical scissors for use in endoscopic surgical procedures commonly include a pair of conventional scissor grips having thumb and finger holes on one or more levers, or include a grip lever mounted at a proximal end of a slender body that is disposed to extend through a lumen between proximal and distal ends of a cannula. Scissor blades pivotally mounted at the distal end of the slender body undergo relative shearing movements in response to sliding movement of a rod or wire within the slender body under control of the manually-manipulated scissor grips at the proximal end. However, such scissor grips are commonly shaped to fit right hand thumb and forefinger for movement in a substantially vertical plane and are not readily conducive to convenient manual manipulation in other orientations that may be required in order to align the scissor blades at the distal end of the slender body for a particular surgical procedure. In addition, the scissor grips include substantial bulk in order to fit an average span of thumb and forefinger of a surgeon, which bulk becomes objectionable during surgical procedures performed in confined quarters and commonly interferes with other instruments and attachments that also emanate from the proximal end of a cannula that is configured for such surgical procedures.

SUMMARY OF THE INVENTION

In accordance with the illustrated embodiment of the present invention, surgical scissors include scissor blades mounted at the distal end of a slender, flexible body for manipulation under control of a single lever mounted at the proximal end of the slender body. The lever is supported in a slender housing of low profile that is attached to the elongated body of the surgical scissors. The lever provides substantial mechanical advantage and need only be actuated fore and aft in substantially normal alignment with the elongated body, using thumb or fingers of either hand while the housing is disposed in any convenient orientation, thereby greatly enhancing the versatility of the scissors as a surgical instrument. In addition, the scissor blades may also contain electrodes or heater elements for supplying energy from external sources to cauterize as well as shear tissue at a remote surgical site in a patient. In one embodiment, the housing and components of the surgical scissors are fabricated to facilitate rapid assembly and ergonomic considerations. Half-shell segments of the housing are disposed to receive sub assemblies that comprise the surgical scissors, and are assembled in mating configurations to constrain the components and complete the surgical scissors.

DESCRIPTION OF THE INVENTION

Figure 1:
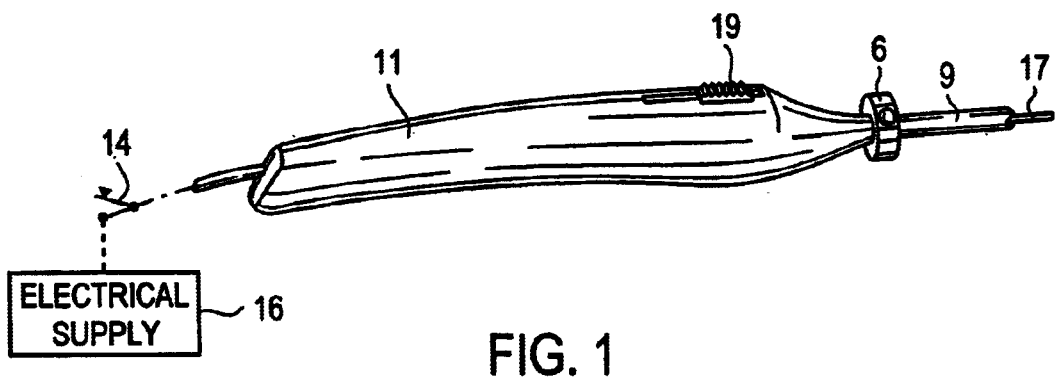
FIG. 1 is a perspective view of one embodiment of the surgical scissors according to one embodiment of the present invention.
Figure 3:
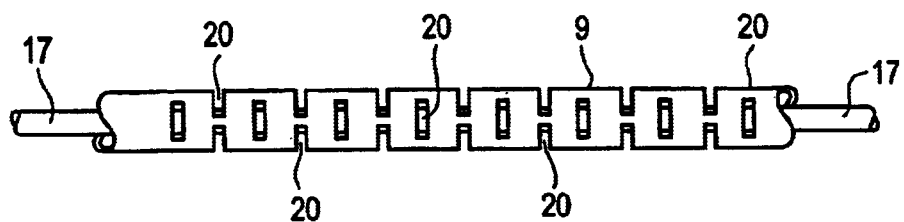
FIGS. 3, 4 and 5 are pictorial views of alternative embodiments of flexible bodies.

Referring now to the illustrated embodiment of FIG. 1, there is shown surgical scissors including an elongated slender body 9 attached at the proximal end thereof to housing 11. The distal end of the body 9 pivotally supports a pair of scissor blades 13, 15, as illustrated in FIG. 3, for undergoing relative shearing movement of the blades in response to pushing (or pulling) of the rod 17 within the hollow, slender body 9. A supply 16 of electrical signal is connected to the scissor blades 13, 15 via switch 14 and connectors, as described later herein, to implement electrocautery procedures in conventional manner.

Figure 2:
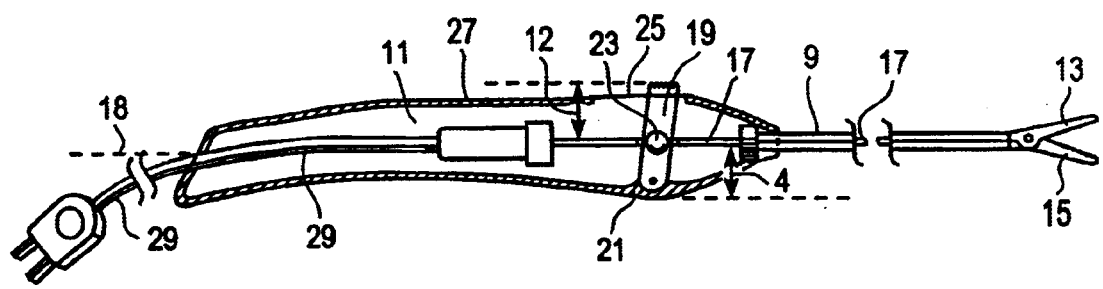
FIG. 2 is a pictorial cut-away view of the housing of the scissors in the embodiment of FIG. 1.

Referring now to FIG. 2, there is shown a pictorial cut-away sectional view of the housing 11 attached to the slender body 9 and pivotally supporting a lever 19 for relative rotation about pivot 21 in a vertical plane (optionally aligned with the vertical plane of pivotal rotation of the blades 13, 15). The housing 11 may be attached to the slender body by a clamping collar 6, as shown in FIG. 1, or by press fit, or by other conventional technique. The lever 19 is pivotally connected 23 to the rod 17, and protrudes from the housing 11 to provide a finger or thumb actuator for movement within an elongated slot 25 in an upper wall 27 of the housing 11. Thus, movement of the actuator and lever 19 forward (e.g., toward body 9) within slot 25 in the housing 11 imparts forward sliding movement of the rod 17 within the body 9. Rod 17 is mechanically coupled to one or both scissor blades 13, 15 in conventional manner either to close with shearing motion in response to forward movement of rod 17, or alternatively, to open in response to such rod movement. Retracting the actuator and lever 19 within the slot 25 in the housing 11 (i.e., away from body 9) effects the opposite movement of the scissor blades 13, 15 than as described above for forward movement of the rod 17 in each alternative embodiment. Alternatively, a pivot axis 21 may be provided on lever 19 at a location thereon intermediate the exposed finger mount and the pivotal connection 23 in order to reverse the relative movements of the rod 17 and lever 19 in conventional manner. Of course, the actuator may be mounted to slide along longitudinal tracks in the housing 11 to facilitate forward and rearward movements of the rod 17 coupled thereto. Alternatively, an encircling actuator ring or collar exposed about the housing 11 may be mounted for sliding movement along a portion of the length of the housing 11 and may be coupled to lever 19 to facilitate identical access to the actuator in all rotational orientations of the housing 11 and body 9 about the elongated axis of the body 9. In each embodiment of a lever actuator according to the present invention, the relative lengths of the lever 19 to a pivot 21 and of the pivoted connection 23 to the pivot 21 are selected to provide mechanical advantage of lever movement to rod movement in order to provide convenient finger-manipulable actuation of the scissor blades 13, 15 at the distal end of body 9.

Figure 7:
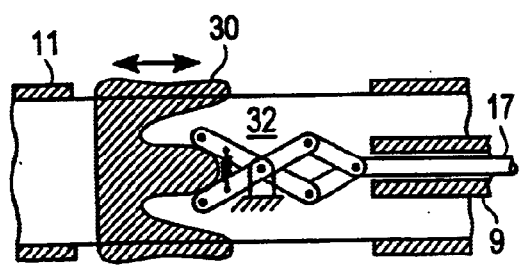
FIGS. 7 and 8 are pictorial sectional views of coupling mechanisms for effecting sliding movements with mechanical force and movement advantage.
Figure 8:
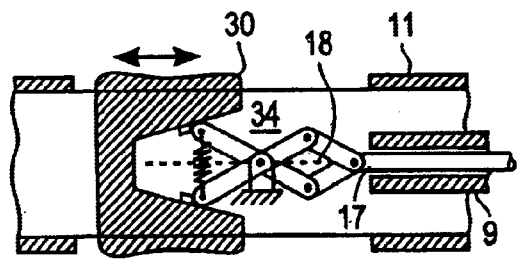

The slender, generally concentric configuration of the housing 11 relative to the elongated body 9 greatly facilitates rotationally positioning the body 9 within a lumen of a cannula as desired to position the scissor blades 13, 15 relative to tissue at a remote surgical site, without significant impediments imposed by any protrusions from the housing 11. Significantly, the generally concentric configuration of the housing 11 and the associated actuator lever 19 mounted therein greatly facilitates easy access to, and manipulation of, the actuator 19 with any finger or thumb of either hand while the housing 11 is in any rotational orientation about the elongated axis of the body 9. As illustrated in the pictorial sectional view of FIGS. 7 and 8, a collar or peripheral ring 30 may be disposed to slide along a portion of the length of the housing 11 in response to finger or thumb manipulation in any orientation of the housing 11 about the central axis of the body 9. Coupling mechanisms 32, 34 may be mounted in the housing 11 to transform the sliding movement of the ring 30 to sliding movement of rod 17, but with mechanical advantage of greater movement of the ring 30 (and hence less force) in relation to the movement of the rod 17. Generally, lateral extensions or protrusions 12, 4 of the housing 11 relative to the elongated axis 18 of the slender body 9, as illustrated in FIG. 2, are within a range of about 1–4 cm.

With reference to FIGS. 1–3, the slender body 9 may be formed as a tightly-wound spring surrounding flexible rod 17 that is slidable within the body 9. Such structure resembles conventional Bowdin cable for motion transfer within a flexible but incompressible sheath.

Figure 4:
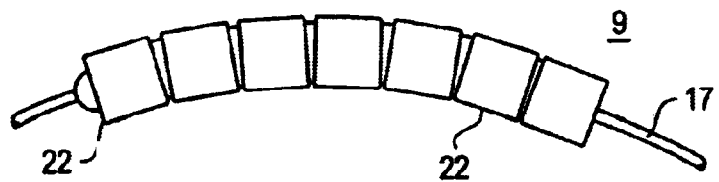
Figure 5:
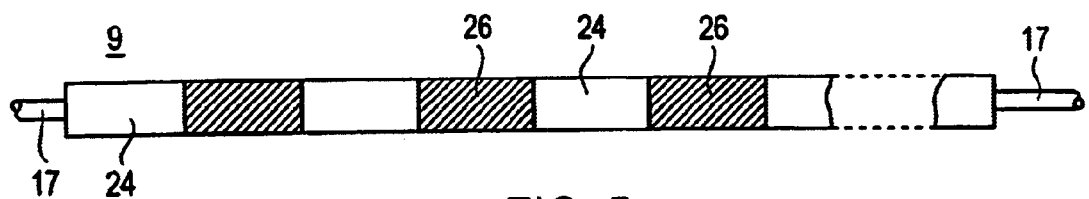
Figure 6:
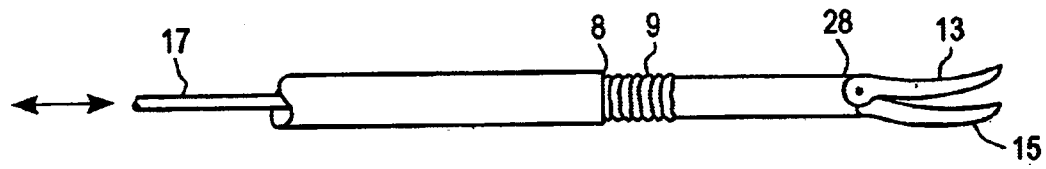
FIG. 6 is a perspective view of scissor blades pivotally mounted on the distal end of an elongated body.

Referring now to FIGS. 3, 4 and 5, there are shown alternative embodiments of flexible bodies 9 that are substantially incompressible longitudinally but that are laterally flexible to accommodate surgical procedures. Specifically, as illustrated in FIG. 3, a thin-walled tube of bio-inert material such as stainless steel or polymer material includes lateral slots or apertures 20 disposed in spaced alternate orthoginal orientations along the length of the body to promote lateral bending flexibility but to retain axial or longitudinal rigidity, as flexible rod 17 slides or rotates within the central bore of the body 9. In the embodiment illustrated in FIG. 4, the body comprises a plurality of hollow bead-like segments 22 that are formed with mating hemispherical and concave ends and that are assembled over a selected length to form the laterally flexible but longitudinally rigid elongated body 9 with the flexible rod 17 disposed within the hollow central bore of the segments 22. As illustrated in the alternate embodiments of FIG. 5, the body 9 may be formed as a plurality of alternating rigid segments 24 and laterally flexible segments 26 (e.g., tightly-wound wire coil spring) with rod 17 disposed to slide and/or rotate within the central bore through the segments 24, 26. As shown in FIG. 6, the body 9 may include a tightly-wound wire coil spring extending between distal and proximal ends of the body 9. In each of the embodiments illustrated in FIGS. 1 through 6, the body 9 may be covered by a layer 8 of bio-inert flexible material such as latex or polypropylene to inhibit incursion of tissue and fluids into the body 9 during surgical procedures.

Referring now to FIG. 6, the perspective view of the distal end of the body 9 illustrates the orientation of scissor blades 13, 15 disposed about pivot axis 28 to open and close in response to relative movement of the rod 17 with respect to the body 9. For translational movement of the rod 17 within body 9 associated with forward and rearward movement of lever 19 within housing 11, conventional linkage between rod 17 and scissor blades 13, 15 within the distal end of the body 9 transforms the longitudinal movements of the rod 17 to scissor-like rotations of the blades 13, 15 about the pivot axis 28 between open and closed positions. Of course, one or more wires may also be used instead of rod 17 to link between actuator 19 and blades 13, 15 to slidably operate within the body 9 in tension, for opening or closing the blades 13, 15 about the common pivot axis of the blades.

Referring now to FIGS. 1, 2 and 5, electrical connections 29 may be made to the scissor blades 13, 15 in conventional manner using rod 17 as one electrical conductor and the outer body 9 insulated from the rod 17 as another electrical conductor, or otherwise as by a pair of conductors within body 9, to supply high voltage to insulated scissor blades 13, 15 for sparking cauterization of tissue, or to supply high electrical current to heaters disposed on the scissor blades 13, 15 for effecting hemostasis via thermal coagulation at a remote surgical site.

Of course, various embodiments of the present invention may include components such as the actuator 19 and housing 11 in half-shell segments and rod 17 and body 9 and pivot 23 and electrical connections that all conveniently snap together in accordance with contemporary manufacturing techniques and component designs.

In operation, the surgical scissors of the present invention may be inserted into a lumen of an elongated cannula that is disposed within an anatomical space which is formed in tissue adjacent the saphenous vein of a patient. The slender and flexible body 9 of the scissors is slidable within the lumen to facilitate selectively extending the scissor blades 13, 15 from the distal end of the cannula into operational position. Specifically, the scissor blades 13, 15 may be relatively rotated about a common pivot axis into open position in response to finger or thumb actuation of the actuator 19 for longitudinal movement in one direction along the housing 11. The scissor blades 13, 15 in open configuration may be positioned about a lateral branch vessel of the saphenous vein, with the aid of endoscopic viewing, and then operated as scissors into closed configuration to shear or ligate the vessel in response to finger or thumb actuation of the actuator 19 for longitudinal movement in opposite direction along the housing 11. In addition, at least one electrode formed on, or otherwise comprising one of the blades 13, 15 may be selectively electrified from electrical source 16 upon actuation of foot-activated or finger-activated switch 14 to provide electrocauterization of the vessel or adjacent tissue sheared by the scissor blades 13, 15. The blades may be curved in mating array to facilitate shearing action on vessels substantially laterally or longitudinally oriented relative to the elongated axis of the body 9. Upon completion of shearing and/or electrocauterization procedures at a surgical site in patient's tissue, the blades 13, 15 may be closed and slid back into and through the lumen of the cannula for removal from the surgical site via the proximal end of the cannula.

The surgical scissors of the present invention greatly facilitates manual access to, and manipulation of, remote scissor blades via an actuating lever that provides mechanical advantage and that is compactly mounted for longitudinal movement within a slender housing. In this configuration, the surgical scissors with associated housing and actuating lever take up minimal space about the proximal end of a cannula within which the slender body of the surgical scissors may be positioned. Various shapes and features may be incorporated into the handle and actuator and slender body and scissor mechanism to promote ergonomic considerations and facilitate rapid manufacture and assembly.

Figure 9:
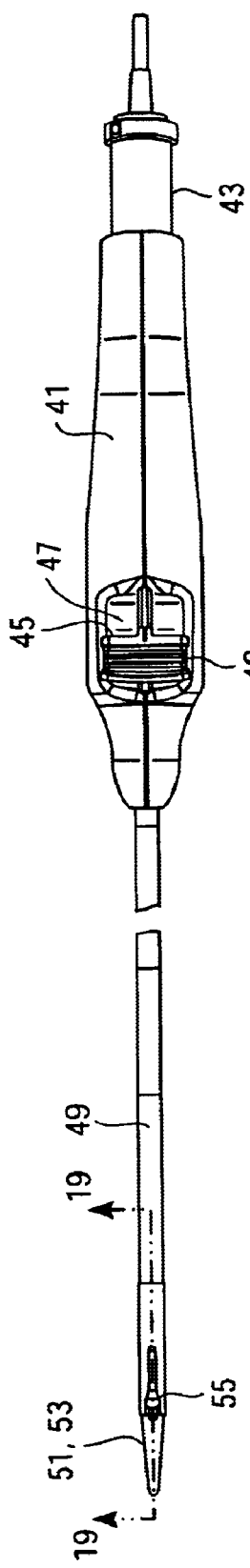
FIG. 9 is a top view of an embodiment of the surgical scissors.
Figure 10:
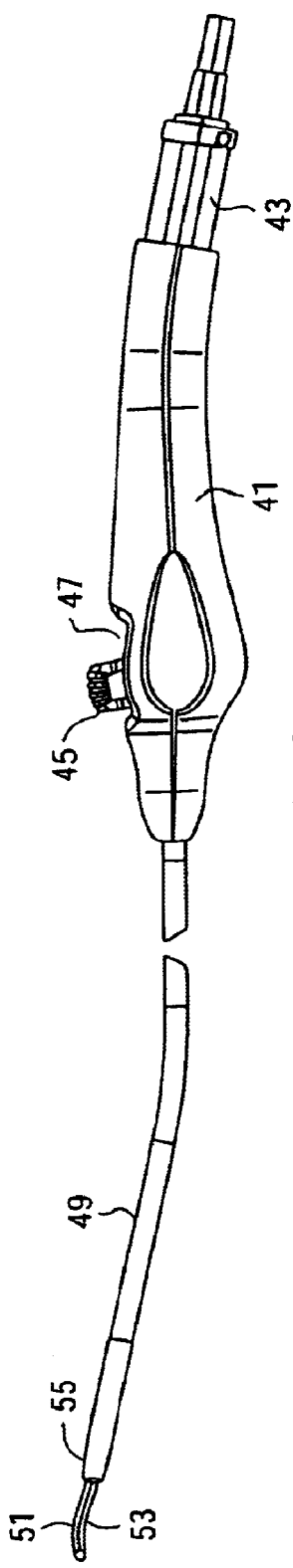
FIG. 10 is a side view of the surgical scissors of FIG. 9.
Figure 11:
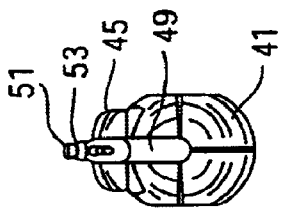
FIG. 11 is a distal end view of the surgical scissors of FIG. 9.

Specifically, as illustrated in the top, side and end views of FIGS. 9–11, the housing 41 supports the slender elongated body 49 attached thereto near the forward end of the housing 41, and includes an electrical connector 43 attached thereto near the rearward end of the housing 41. An actuating level 45 is mounted in the housing 41 to rotate fore and aft within the recess 47 in the top of the housing 41, and the lever 45 may include surface striations 48 or other surface treatments to promote anti-slip finger placement by a user during actuation of the lever 45. The scissor blades 51, 53 are mounted at the distal end of the slender body 49 to rotate about a common pivot axis 55, as more fully described later herein. The slender body 49 is laterally flexible and resilient but is substantially axially incompressible to promote repeatable, predictable control over scissor motions of the blades 51, 53 in response to fore and aft movements of the actuator lever 45, in a manner as previously described herein.

Figure 13:
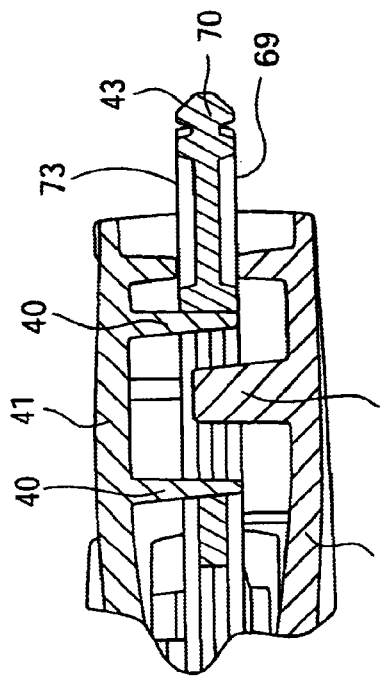
FIG. 13 is a top sectional view of the electrical connector at the rear end of the housing of the surgical scissors of FIG. 9.
Figure 12:
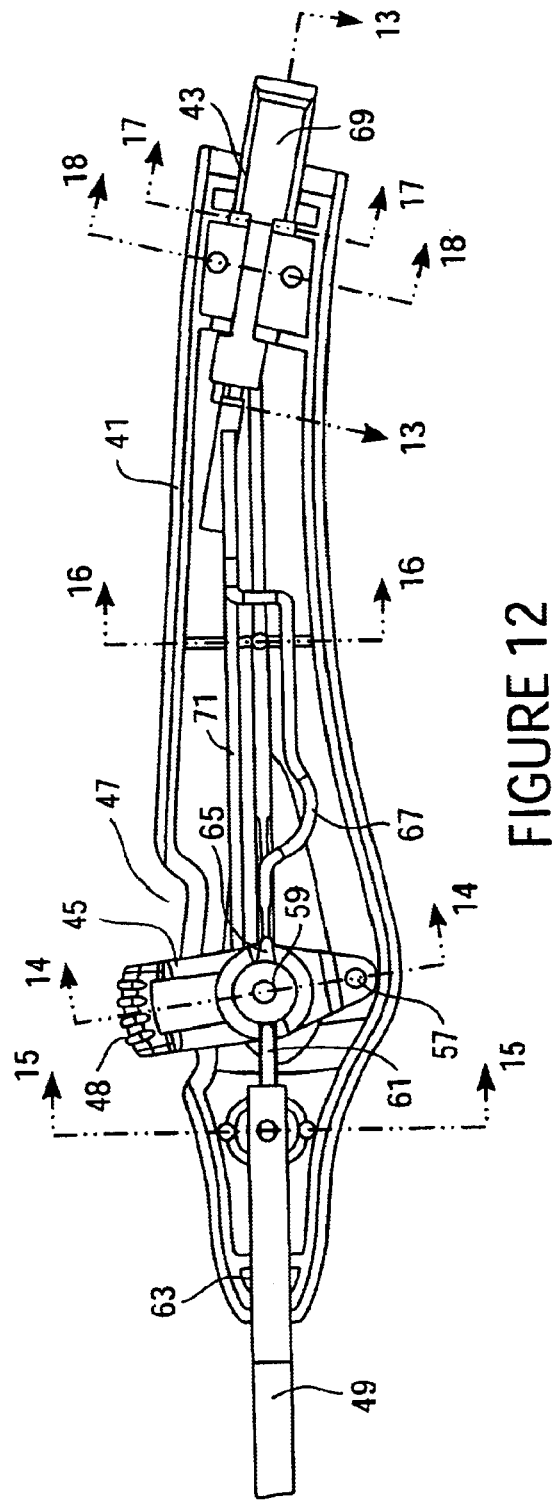
FIG. 12 is a cutaway side view of the assembly within the housing of the surgical scissors of FIG. 9.

Referring now to FIG. 12, there is shown a side cutaway view of the embodiment of FIGS. 9–11. The housing 41 is structured in half-shell configuration to facilitate assemblage of internal components prior to attachment thereto of a mating half-shell of the housing 41 to captivate the assembled components and complete the fabrication. Specifically, the actuating lever 45 is mounted on pivot axis 57 for rotation thereabout in fore and aft motion in the recess 47. A pivot 59 carried on the lever 45 pivotally couples to push rod 61 that is slidably disposed within the slender body 49 which, in turn, is affixed to the housing 41 by clamping between half-shells 63, or by gluing, or the like. In addition, the pivot 59 may carry an electrical connector 65 and an attached flexible conductor 67 for electrically connecting one conductor 69 of the connector 43 to the insulated push rod 61 through the movable pivot 59. Another conductor of the connector 43 may be connected via conductor 71 to a sheath beneath a layer of insulation on the body 49 to provide two electrical conductors and connections from the connector 43 through the housing 41 and body 49 to electrodes on the blades 51, 53 of the scissors at the distal end. As illustrated in the top sectional view of FIG. 13, the connector 43 includes a blade-like insulator 70 with metallic contacts and conductors 69, 73 attached on opposite sides thereof, and with tabs or protrusions 40, 42 in the half shells 41 of the housing extending across the insulator 70 and conductors 69, 73 to retain the connector assembly firmly in place in the assembly within the half shells 41 of the housing.

Figure 15:
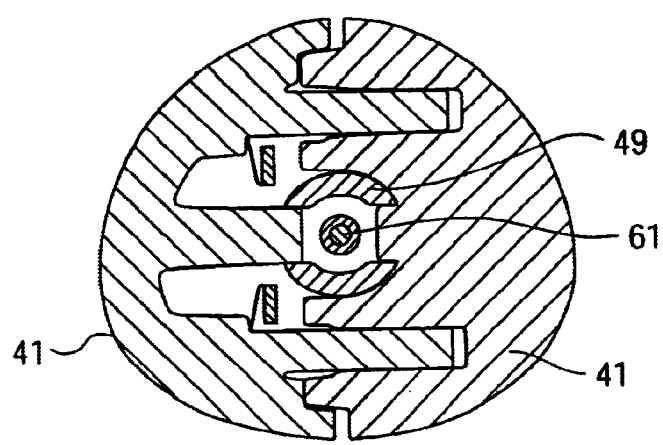
FIGS. 14–18 are sectional views of the assembly at selected locations within the housing of the surgical scissors of FIG. 9.
Figure 14:
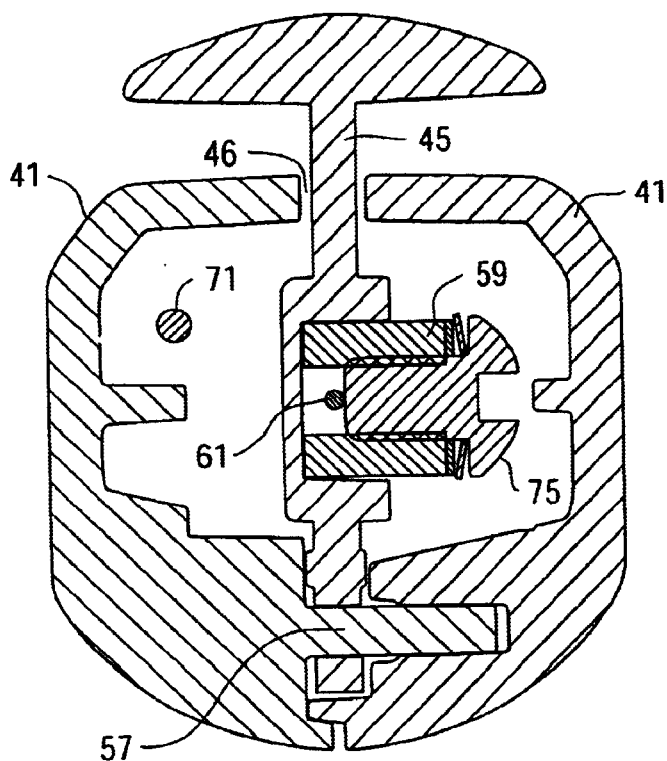

Referring now to FIG. 14, there is shown a sectional view of the housing and lever assembly showing the pivotal mounting 57 of the lever 45. Specifically, the pivot 57 for lever 45 is formed as a protrusion that extends between half shells 41 of the housing that includes a slit 46 aligned fore and aft in the upper recess 47 of the housing 41 to accommodate pivotal movement of the lever 45 about the pivot 57. The movable pivot 59 carried on the lever 45 at a location thereon intermediate the pivot 57 and the finger surface 48 is formed using a bolt attachment 75 of the push rod 61 and electrical connector 65. As illustrated in the cross sectional view of FIG. 15, the slender body 49 may be clamped between half shells 41 of the housing near the forward end thereof, with conductor 71 connected to the slender body, and various tabs or protrusions within and between half shells 41 retaining the assembly intact.

Figure 17:
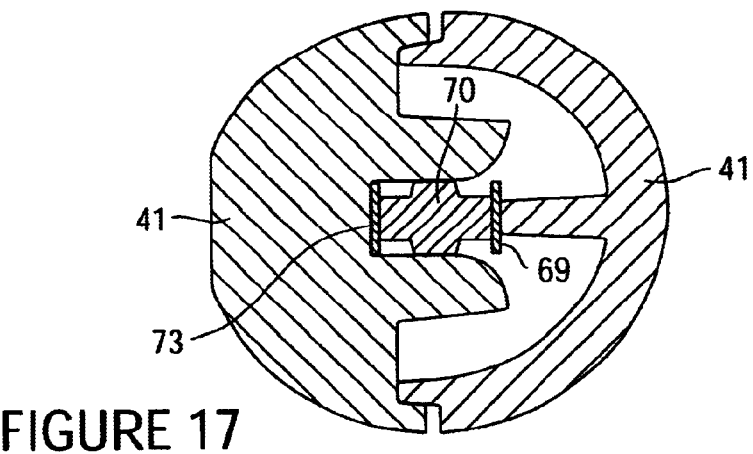
Figure 16:
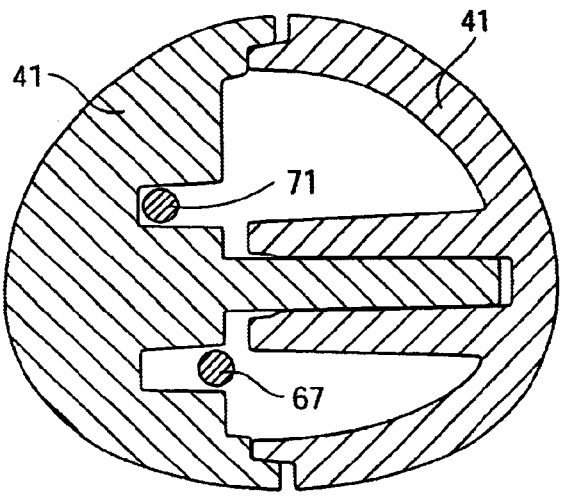
Figure 18:
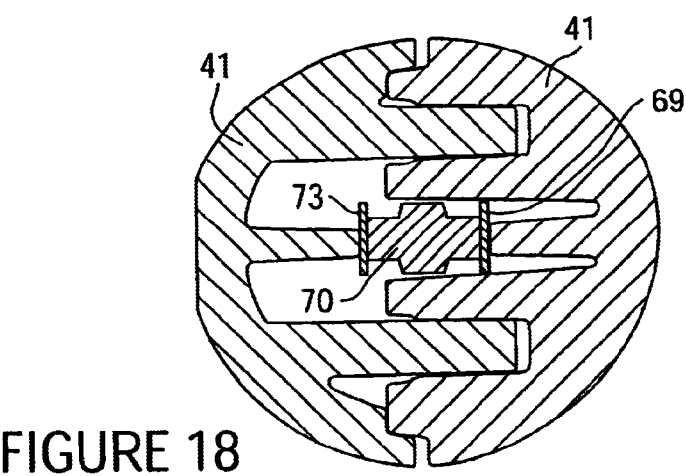

The cross sectional views of the housing illustrated in FIGS. 16–18 show various configurations of the half shells 41, respectively, at an intermediate location and at connector locations near the rearward end of housing 41 at which various tabs and protrusions between half shells 41 of the housing retain the assembly intact.

Figure 19:
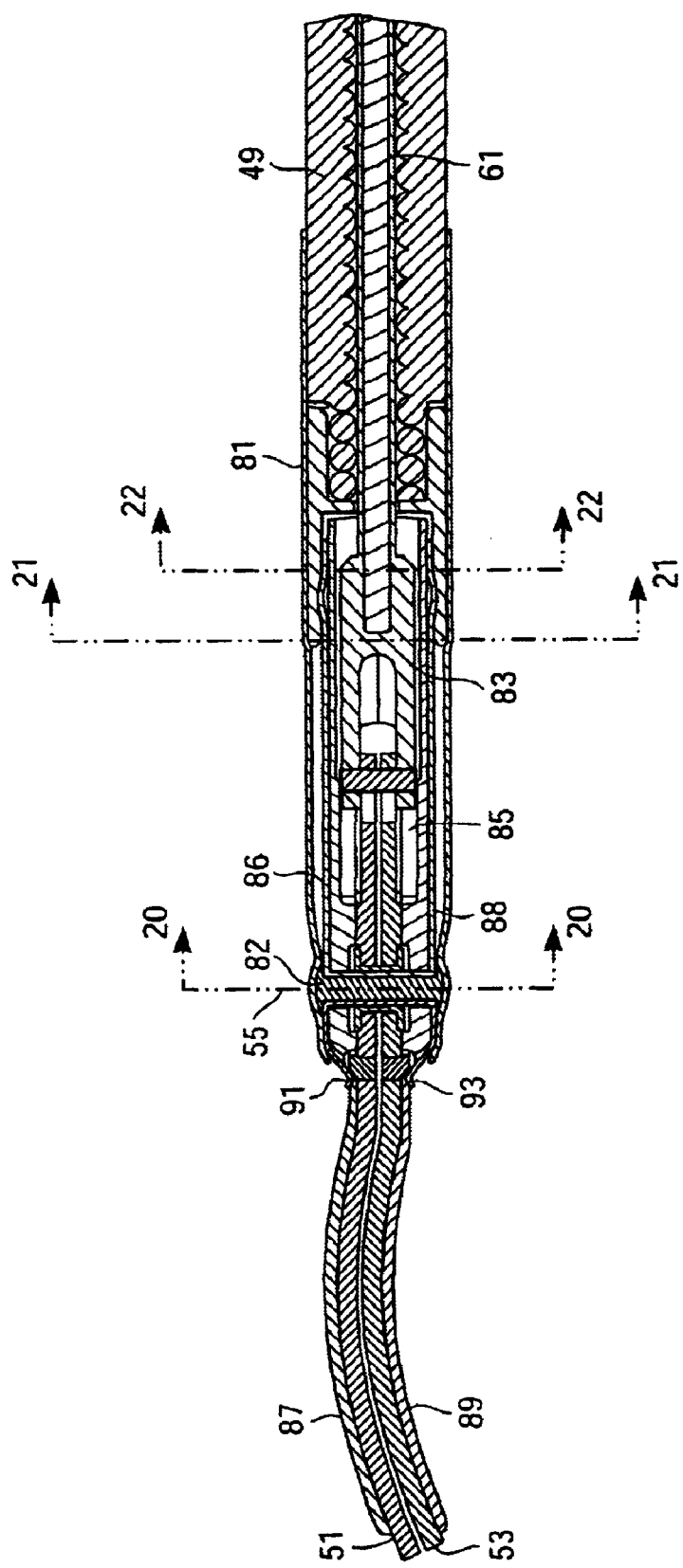
FIG. 19 is a side sectional view of the surgical scissors hear the distal end thereof.
Figure 22:
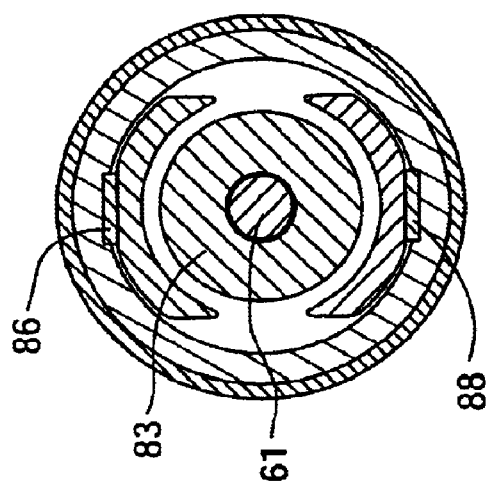
FIGS. 20–22 are sectional views of the assembly at various locations near the distal end.
Figure 21:
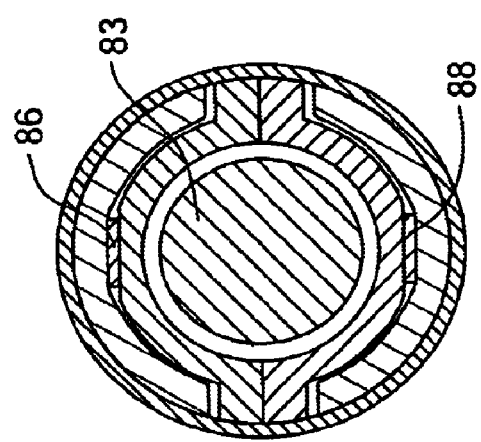
Figure 20:
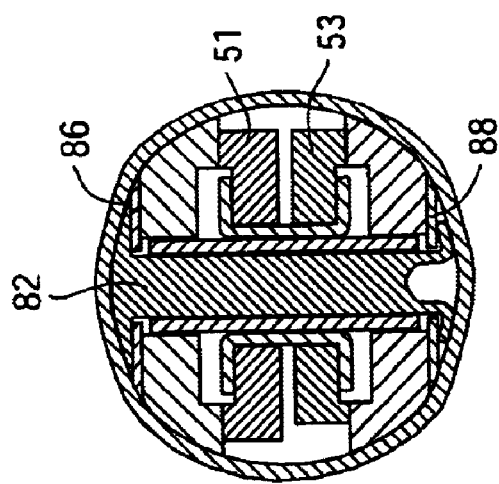

Referring now to FIG. 19, there is shown a side sectional view of the scissor assembly 51, 53 at the distal end of the slender body 49. A ferrule 81 affixed to the end of the flexible slender body 49 (e.g., a wire-wound sheath) supports a pivot 82 for the scissor blades 51, 53 and houses a collet 83 attached to the push rod 61 as a portion of the mechanical coupling 85 to transform translational movement of push rod 61 relative to the body 49 into pivotal scissor-like movement of blades 51, 53 about the pivot axis 55 of the pivot 82. In addition, the blades 51, 53 each include an outer layer of insulation 87, 89 which carries a conductive layer or foil thereon that is insulated from the blades 51, 53 by the insulation 87, 89, and that is connected to the electrical conductors 86, 86 via contacting spring clips 91, 93. The conductive layers thus serve as electrodes near the shearing edges of the blades 51, 53. FIG. 20 is a cross sectional view of the scissor assembly about the pivot 82, and FIGS. 21 and 22 are cross sectional views of the collet and ferrule assemblies attached to the distal ends of the body 49 and push rod 61.

Therefore, the surgical scissors of the present invention operate with compact mechanisms to provide motion and force advantage within a slender body and housing of low profile and non-directional angular orientation about the axis of the body and housing. Fore and aft movement of a lever within a slender housing provides leverage and force advantage to facilitate finger and thumb operation of remote scissor blades at the distal end of an elongated flexible body of slender cross section. Electrodes carried on the scissor blades promote unipolar or bipolar electrocautery via electrocautery signals supplied through the slender body and attached housing. The surgical scissors may be conveniently fabricated within half shells of the housing which are configured in mating relationship to retain assemblies and confine the operating lever within an instrument of low profile.

We claim:

1. Surgical scissors comprising:
   an elongated substantially longitudinally incompressible body of spiral-wound wire forming contiguous adjacent convolutes having lateral flexibility and having distal and proximal ends;
   an actuator rod having lateral flexibility slidably disposed within the body between the distal and proximal ends;
   at least one of a pair of scissor blades pivotally mounted on the distal end of the body for relative shearing movement therebetween in response to sliding movement of the actuator rod coupled thereto;
   a housing attached to the proximal end of the body, the housing including mating shells having protrusions therein for traversing mating engagements of the shells;
   a lever mounted on a protrusion for pivotal movement thereabout in longitudinal orientation relative to the elongated body;
   a linkage coupling the lever to the actuator rod for imparting sliding movement thereto with mechanical advantage in response to pivotal movement of the lever about the protrusion;
   an electrical connector disposed near a rearward end of the housing including a pair of conductors; and
   electrical connections including the actuator rod and the wire spiral insulated from each other and connecting the pair of conductors to electrodes disposed on the pair of the scissor blades.

2. Surgical scissors comprising:
   an elongated substantially longitudinally incompressible body of spiral-wound wire forming contiguous adjacent convolutes having lateral flexibility and having distal and proximal ends;
   an actuator rod having lateral flexibility slidably disposed within the body between the distal and proximal ends;
   at least one of a pair of scissor blades pivotally mounted on the distal end of the body for relative shearing movement therebetween in response to sliding movement of the actuator rod coupled thereto;
   a housing attached to the proximal end of the body, the housing including mating shells having protrusions therein for traversing mating engagements of the shells;
   a lever mounted on a protrusion for pivotal movement thereabout in longitudinal orientation relative to the elongated body; and
   a linkage coupling the lever to the actuator rod for imparting sliding movement thereto with mechanical advantage in response to pivotal movement of the lever about the protrusion.

3. Surgical scissors comprising:
   an elongated substantially longitudinally incompressible body having a plurality of contiguous elements providing lateral flexibility between elements and having distal and proximal ends;
   an actuator rod having lateral flexibility slidably disposed within the body between the distal and proximal ends;
   at least one of a pair of scissor blades pivotally mounted on the distal end of the body for relative shearing movement therebetween in response to sliding movement of the actuator rod coupled thereto;
   a housing attached to the proximal end of the body, the housing including mating shells having protrusions therein for traversing mating engagements of the shells;
   a lever mounted on a protrusion for pivotal movement thereabout in longitudinal orientation relative to the elongated body; and
   a linkage coupling the lever to the actuator rod for imparting sliding movement thereto with mechanical advantage in response to pivotal movement of the lever about the protrusion.

4. Surgical scissors comprising:
   an elongated substantially longitudinally incompressible body having a plurality of contiguous elements providing lateral flexibility between elements and having distal and proximal ends;
   an actuator rod having lateral flexibility slidably disposed within the body between the distal and proximal ends;
   at least one of a pair of scissor blades pivotally mounted on the distal end of the body for relative shearing movement therebetween in response to sliding movement of the actuator rod coupled thereto;
   a housing attached to the proximal end of the body, the housing including mating shells having protrusions therein for traversing mating engagements of the shells;
   a lever mounted on a protrusion for pivotal movement thereabout in longitudinal orientation relative to the elongated body;
   a linkage coupling the lever to the actuator rod for imparting sliding movement thereto with mechanical advantage in response to pivotal movement of the lever about the protrusion;
   an electrical connector disposed near a rearward end of the housing including a pair of conductors; and
   electrical connections including the actuator rod connecting the pair of conductors to electrodes disposed on the pair of the scissor blades.

5. Surgical scissors according to claim 4 comprising:
   a sheath of electrically insulating material overlaying the contiguous elements of the elongated body substantially between the proximal and distal ends thereof.

6. Surgical scissors comprising:
   an actuator rod having lateral flexibility and substantial longitudinal rigidity between the distal and proximal ends;
   a plurality of concentric elements contiguously disposed overlaying the actuator rod and having substantial longitudinal incompressibility and lateral flexibility between distal and proximal ends thereof;
   at least one of a pair of scissor blades pivotally mounted on the distal end of the body for relative shearing movement therebetween in response to sliding movement of the actuator rod coupled thereto;
   a housing attached to the proximal end of the body, the housing including mating shells having protrusions therein for traversing mating engagements of the shells;
   a lever mounted on a protrusion to extend outside the housing for pivotal movement about the protrusion in longitudinal orientation relative to the elongated body; and
   a linkage coupling the lever to the actuator rod for imparting sliding movement thereto with mechanical advantage in response to pivotal movement of the lever about the protrusion.

7. Surgical scissors according to claim 6 in which the linkage is coupled to the actuator rod at a location intermediate the length of the lever.

* * * * *